United States Patent
Khodakovskaya et al.

(10) Patent No.: US 9,675,078 B2
(45) Date of Patent: *Jun. 13, 2017

(54) METHOD OF DELIVERY OF BIO-ACTIVE AGENTS TO PLANT CELLS BY USING NANO-SIZED MATERIALS AS CARRIERS

(71) Applicant: BOARD OF TRUSTEES OF THE UNIVERSITY OF ARKANSAS, Little Rock, AR (US)

(72) Inventors: Mariya Khodakovskaya, Little Rock, AR (US); Mohamed Hassen Lahiani, North Little Rock, AR (US); Alexandru S. Biris, Little Rock, AR (US)

(73) Assignee: BOARD OF TRUSTEES OF THE UNIVERSITY OF ARKANSAS, Little Rock, AR (US)

(*) Notice: Subject to any disclaimer, the term of this patent is extended or adjusted under 35 U.S.C. 154(b) by 52 days.

This patent is subject to a terminal disclaimer.

(21) Appl. No.: 14/683,978

(22) Filed: Apr. 10, 2015

(65) Prior Publication Data
US 2015/0208663 A1 Jul. 30, 2015

Related U.S. Application Data

(63) Continuation-in-part of application No. 14/513,744, filed on Oct. 14, 2014.

(60) Provisional application No. 62/082,482, filed on Nov. 20, 2014, provisional application No. 61/891,006, filed on Oct. 15, 2013.

(51) Int. Cl.
| | |
|---|---|
| *A01N 59/16* | (2006.01) |
| *A01N 37/10* | (2006.01) |
| *A01N 25/28* | (2006.01) |
| *A01N 25/34* | (2006.01) |

(52) U.S. Cl.
CPC .................. *A01N 59/16* (2013.01)

(58) Field of Classification Search
CPC ................ A01N 59/16; A01N 25/26

USPC .......................................................... 504/323
See application file for complete search history.

(56) References Cited

PUBLICATIONS

Nima, Zeid A. et al., "Circulating tumor cell identification by functionalized silver-gold nanorods with multicolor, super-enhanced SERS and photothermal resonances", Scientific Reports, vol. 4, Article No. 4752, pp. 1-8, Published: May 9, 2014.

Villagarcia, Hector et al., "Surface Chemistry of Carbon Nanotubes Impacts the Growth and Expression of Water Channel Protein in Tomato Plants", Small, vol. 8, No. 15, pp. 2328-2334, Published online: Apr. 18, 2012.

El-Temsah, Yehia Sayed et al., "Impact of Fe and Ag Nanoparticles on Seed Germination and Differences in Bioavailability During Exposure in Aqueous Suspension and Soil", Wiley Periodicals, Inc., Environmental Toxicology, pp. 42-49, Accepted: Mar. 13, 2010.

Barrena, Raquel et al., "Evaluation of the ecotoxicity of model nanoparticles", Elsevier Ltd., Chemosphere, vol. 75, No. 7, pp. 850-857, Available online: Mar. 4, 2009.

Parry, G., et al., "Complex regulation of the TIR1/AFB family of auxin receptors", PNAS, vol. 106, No. 52, pp. 22540-22545, Dec. 29, 2009.

*Primary Examiner* — Janet Epps-Smith
*Assistant Examiner* — Courtney Brown
(74) *Attorney, Agent, or Firm* — Tim Tingkang Xia, Esq.; Locke Lord LLP

(57) ABSTRACT

A method for regulating properties of a plant, includes: providing a nanoagent having at least one nanocomposite; and delivering the nanoagent to the plant. The nanocomposite has at least one gold nanorod, a silver layer coated on an outer surface of the gold nanorod, a pegylated layer coated on the silver layer, and an active layer conjugated to the pegylated layer. The silver layer includes silver nanoparticles. The pegylated layer includes at least one of thiolated polyethylene glycol (HS-PEG), thiolated polyethylene glycol acid (HS-PEG-COOH) and HS-PEG-NHx. The active layer includes at least one bio-active agent configured to interact with the plant. The bio-active agent can be 2,4-dichlorophenoxyacetic acid (2,4-D).

17 Claims, 4 Drawing Sheets

202 — Providing a nanoagent

206 — Delivering the nanoagent to a plant

210 — Detecting and Monitoring conditions of the target plant

FIG. 2

METHOD OF DELIVERY OF BIO-ACTIVE AGENTS TO PLANT CELLS BY USING NANO-SIZED MATERIALS AS CARRIERS

CROSS-REFERENCE

This application claims priority to and the benefit of, pursuant to 35 U.S.C. §119(e), U.S. provisional patent application Ser. No. 62/082,482, filed on Nov. 20, 2014, entitled "METHOD OF DELIVERING OF BIO-ACTIVE AGENTS TO PLANT CELLS BY USING GOLD NANO-PARTICLES AS CARRIERS," by Mariya Khodakovskaya, which is incorporated herein by reference in its entirety.

This application is also a continuation-in-part of U.S. patent application Ser. No. 14/513,744, filed on Oct. 14, 2014, entitled "NANOCOMPOSITES, METHODS OF MAKING SAME, AND APPLICATIONS OF SAME FOR MULTICOLOR SURFACE ENHANCED RAMAN SPECTROSCOPY (SERS) DETECTIONS," by Alexandru S. Biris, Zeid Nima and Yang Xu, which is incorporated herein by reference in its entirety and which claims priority to and the benefit of, pursuant to 35 U.S.C. §119(e), U.S. provisional patent application Ser. No. 61/891,006, filed on Oct. 15, 2013, entitled "MULTICOLOR SERS DETECTION AND IMAGING OF CANCER CELLS IN BLOOD USING SILVER DECORATED GOLD NANOROD," by Alexandru S. Biris, Zeid Nima and Yang Xu, which is incorporated herein by reference in its entirety.

Some references, which may include patents, patent applications and various publications, are cited and discussed in the description of this invention, which includes, among other things, exhibits and drawings, if any. The citation and/or discussion of such references is provided merely to clarify the description of the invention and is not an admission that any such reference is "prior art" to the invention described herein. All references cited and discussed in this specification are incorporated herein by reference in their entireties and to the same extent as if each reference was individually incorporated by reference.

FIELD OF THE INVENTION

The invention relates generally to a method of regulating properties of a plant, and more specifically related to a method of delivering a bio-active agent to a plant using nanoagents as carriers.

BACKGROUND OF THE INVENTION

The background description provided herein is for the purpose of generally presenting the context of the invention. Work of the presently named inventors, to the extent it is described in this background section, as well as aspects of the description that may not otherwise qualify as prior art at the time of filing, are neither expressly nor impliedly admitted as prior art against the invention.

Plant growth regulators are used for regulating conditions of plant, such as cell growth and development of mature plants. However, numbers of limitations of such approach exist. For example, hormonal plant regulators cannot easily be absorbed and transported inside exposed plants. Thus, plant growth regulators can be less efficient in low doses but toxic for plants in higher doses. Additionally, ability of delivery of growth regulators to specific plant organ or plant tissue in a precise manner is limited.

Therefore, a heretofore unaddressed need exists in the art to address the aforementioned deficiencies and inadequacies.

SUMMARY OF THE INVENTION

In one aspect, the invention is directed to a method for regulating properties of a plant. In one embodiment, the method includes providing a nanoagent and delivering the nanoagent to the plant.

The nanoagent may include one or more type of nanocomposites. The nanocomposite includes at least one gold nanorod, a silver layer coated on an outer surface of the gold nanorod, a pegylated layer coated on the silver layer, and an active layer conjugated to the pegylated layer. The silver layer has silver nanoparticles. The pegylated layer includes at least one of thiolated polyethylene glycol (HS-PEG), thiolated polyethylene glycol acid (HS-PEG-COOH) and HS-PEG-NHx. The active layer includes at least one bio-active agent configured to interact with the plant.

In one embodiment, the bio-active agent includes plant growth regulators, proteins, and nucleic acids.

In one embodiment, the bio-active agent includes 2,4-dichlorophenoxyacetic acid (2,4-D) or other auxins, abscisic acid (ABA), cytokinins, ethylene, gibberellins, salicylic acid, nitric oxide, or jasmonates.

In one embodiment, the step of delivering the nanoagent to the plant includes providing a growing medium for plant cells of the plant, seeding the plant cells in the growing medium, and adding the nanoagent to the growing medium.

In one embodiment, the plant includes tomato, tobacco, or cucumber.

In one embodiment, the gold nanorod has an aspect ratio (AR) in a range of about 1-9, a length in a range of about 10-100 nm, and a diameter in a range of about 1-40 nm.

In one embodiment, the silver layer has a thickness in a range of about 0.5-5 nm.

In one embodiment, the nanocomposite further includes a Raman reporter molecule layer disposed between the silver layer and the active layer. The Raman reporter molecule layer includes the Raman reporter molecules that are detectable by surface enhanced Raman spectroscopy (SERS).

In one embodiment, the Raman reporter molecule layer includes 4-mercaptobenzoic acid (4MBA), p-aminothiophenol (PATP), p-nitrothiophenol (PNTP), 4-(methylsulfanyl) thiophenol (4MSTP), or other molecules with unique Raman spectra and intense Raman peak intensities.

In one embodiment, the at least one nanocomposite includes a first nanocomposite, a second nanocomposite, a third nanocomposite, and a fourth nanocomposite. The Raman reporter molecule layer of the first nanocomposite has 4-mercaptobenzoic acid (4MBA). The Raman reporter molecule layer of the second nanocomposite has p-aminothiophenol (PATP). The Raman reporter molecule layer of the third nanocomposite has p-nitrothiophenol (PNTP). The Raman reporter molecule layer of the fourth nanocomposite has 4-(methylsulfanyl) thiophenol (4MSTP)

In one embodiment SERS signal corresponding to each of the first, second, third and fourth nanocomposites is represented by a predetermined color, such that the target of interest, such as a plant or certain portion of the plant or certain type of plant cells, may be accurately determined and easily viewed using multi-color detection.

In one embodiment, the active layer further includes targeting molecules conjugated to the Raman reporter molecule layer or the bio-active agent. The targeting molecules are configured to bind to the plant, certain portion of the plant, certain type of plant cells, or other target of interest.

In one embodiment, the HS-PEG has a molecular weight in a range of about 1.5-15 kilo Dalton (kD) and the HS-PEG-COOH has a molecular weight in a range of about 1-10 kD.

In another aspect, the present invention is directed to a method of regulating properties of a plant. In one embodiment, the method includes providing a nanoagent, and delivering the nanoagent to the plant.

The nanoagent includes one or more types of nanocomposites. The nanocomposite includes a nanostructure formed by at least one nanomaterial, and an active layer conjugated to the nanostructure. The active layer includes a bio-active agent.

In one embodiment, the bio-active agent includes plant growth regulators, proteins, and nucleic acids.

In one embodiment, the bio-active agent includes at least one of 2,4-dichlorophenoxyacetic acid (2,4-D) or other auxins, abscisic acid (ABA), cytokinins, ethylene, gibberellins, salicylic acid, nitric oxide, and jasmonates.

In one embodiment, the step of delivering the nanoagent to the plant includes:
providing a growing medium for plant cells of the plant;
seeding the plant cells in the growing medium; and
adding the nanoagent to the growing medium.

In one embodiment, the plant includes tomato, tobacco, or cucumber.

In one embodiment, the nanomaterial comprises at least one of silver coated gold rods, quantum dots, nanowires, nanotubes, nanofibers, and fullerenes.

In one embodiment, the nanostructure includes at least one gold nanorod, and a silver layer surrounding the at least one gold nanorod. The silver layer includes silver nanoparticles.

In one embodiment, the gold nanorod has an aspect ratio (AR) in a range of about 1-9, a length in a range of about 10-100 nm, and a diameter in a range of about 1-40 nm.

In one embodiment, the silver layer has a thickness in a range of about 0.5-5 nm.

In one embodiment, the nanocomposite further includes a reporter layer disposed between the nanomaterial and the active layer. The reporter layer is detectable by at least one of surface enhanced Raman spectroscopy (SERS), magnetic resonance imaging (MRI), x-ray radiography, computed tomography (CT), and infrared spectroscopy (IR).

In one embodiment, the nanocomposite further includes a pegylated layer disposed between the reporter layer and the active layer. The pegylated layer includes at least one of thiolated polyethylene glycol (HS-PEG), thiolated polyethylene glycol acid (HS-PEG-COOH) and HS-PEG-NHx.

In one embodiment, the active layer further includes targeting molecules configured to bind to at least one cell of the plant.

In one embodiment, the bio-active agent is conjugated to at least one of the pegylated layer and the targeting molecules.

Further areas of applicability of the invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The following figures form part of the present specification and are included to further demonstrate certain aspects of the invention. The invention may be better understood by reference to one or more of these figures in combination with the detailed description of specific embodiments presented herein. The drawings described below are for illustration purposes only. The drawings are not intended to limit the scope of the present teachings in any way.

FIG. 2 shows a flowchart of delivering a nanoagent to a plant according to one embodiment of the invention.

DETAILED DESCRIPTION OF THE INVENTION

Figure 1:
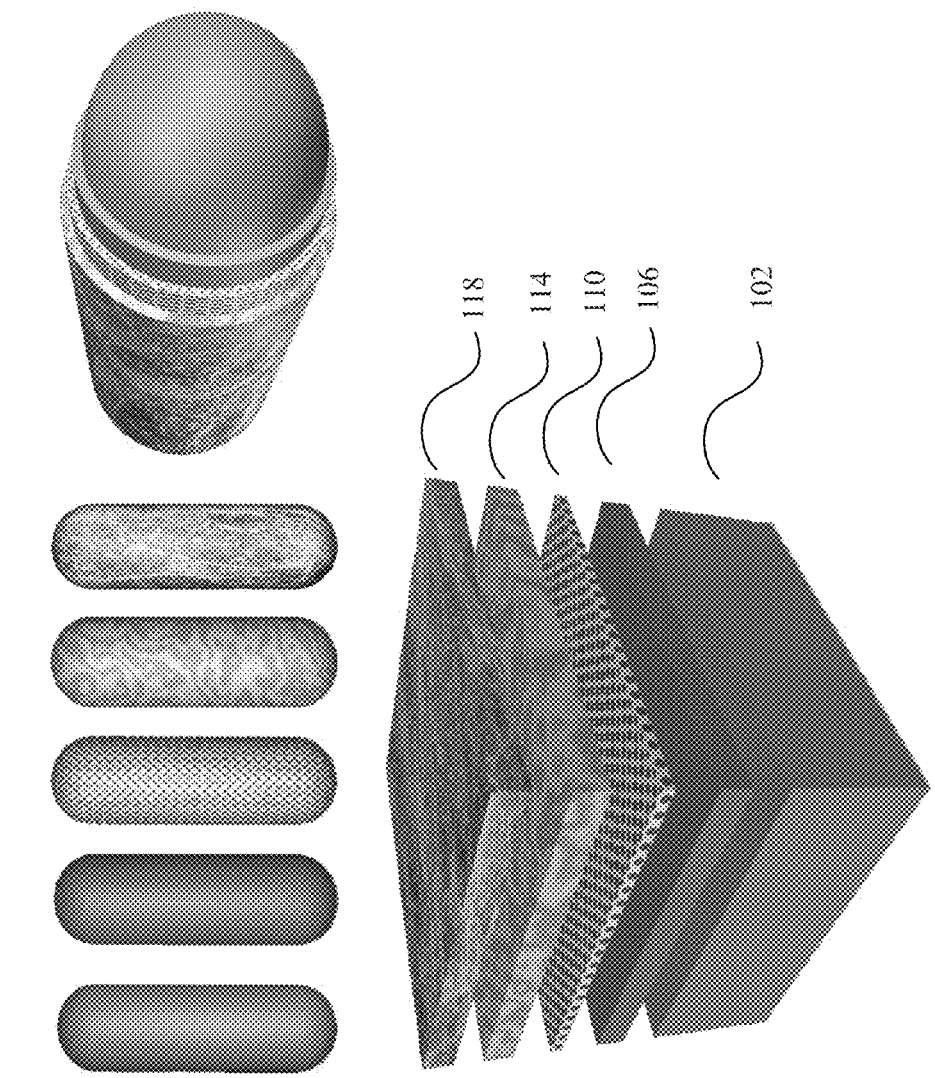
FIG. 1 schematically shows a nanocomposite of a nanoagent according to one embodiment of the invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

As used herein, "around", "about", "substantially" or "approximately" shall generally mean within 20 percent, preferably within 10 percent, and more preferably within 5 percent of a given value or range. Numerical quantities given herein are approximate, meaning that the terms "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the term "4MBA" refers to 4-mercaptobaezoic acid, PNTP is the abbreviation of p-nitrobenzoic acid, PATP is the abbreviation of p-aminobenzoic acid, 4MSTP is the abbreviation of 4-methylsulfanyl thiophenol, and 4APDS is the abbreviation of 4-aminophenyldisulfide.

As used herein, the term "HS-PEG-COOH and HS-PEG" refer to thiolated polyethylene glycol with or without acid terminal, respectively.

As used herein, the term "phosphate buffered saline" or "PBS" refers to a buffer solution commonly used in biological research. It is a water-based salt solution containing sodium phosphate, sodium chloride and, in some formulations, potassium chloride and potassium phosphate. The osmolarity and ion concentrations of the solutions match those of the human body (isotonic).

Overview of the Invention

There is a demand for the development of safe and efficient technologies for the delivery of bio-active agents including pesticides, proteins, and nucleic acid inside plant organisms. Such technologies could be beneficial for agriculture and horticulture, as well as plant genetic engineering. Here, we demonstrate, for the first time to the best of our knowledge, that gold nanomaterial covered with silver and fused with plant growth regulator have the ability to deliver auxin growth regulator (2,4-D) to tobacco cells, resulting in a significant enhancement of the tobacco cell culture (callus culture) growth compared with regular growth conditions (medium with only 2,4-D). This observation can have a role of foundation for development of new nanomaterial-plant growth regulators delivery systems.

Implementations and Examples of the Invention

Without intend to limit the scope of the invention, further exemplary procedures and preliminary experimental results of the same according to the embodiments of the invention are given below.

In one aspect, the present invention is directed to a biocompatible nanoagent for detecting, and monitoring a target of interest, such as at least one plant cell by SERS, and treating the target of interest by the bio-active agents attached to the nanoagent. In certain embodiments, the biocompatible nanoagent includes one or more nanocomposites.

FIG. 1 schematically shows a nanocomposite of a nanoagent according to one embodiment of the invention. Referring to FIG. 1, the nanocomposite has a shape of a rod and the rod has multiple layers stacked one by one, and the outer layers enclose the inner layers. Each of the nanocomposite 100 includes a core 102, a shell 106 wrapped around the core 102, a reporter layer 110 assembled on the shell 106, a binding layer 114 coated on the reporter layer 110, and an active layer 118 conjugated to the binding layer 114.

In certain embodiments, the core 102 is a gold nanorod (AuNR). The aspect ratio (AR) is defined as the ratio of the length of the AuNR to the diameter of the AuNR. In one embodiment, the AR of the AuNR 102 may be in the range of about 0.3-30, and the length and diameter of the AuNR 102 may be in the range of about 3.6-360 nanometer (nm) and about 1.2-120 nm, respectively. In one embodiment, the AR of the AuNR 102 is in the range of about 1-9. In one embodiment, the precise AR of the AuNR 102 is in the range of about 2-5. In one embodiment, the precise AR of the AuNR 102 is in the range of about 2.77-3.23, or about 3±0.23. In one embodiment, the length and diameter of the AuNR 102 may be in the range of about 10-100 nm and about 1-40 nm, respectively. In one embodiment, the particle length and diameter of the AuNR 102 may be approximately 36±0.80 nm and 12±0.41 nm, respectively. In one embodiment, these two dimensions are adequate to form two kinds of surface plasmon modes: a weak one around 520 nm transvers mode, and a very strong longitudinal plasmon around 766 nm. The longitudinal surface plasmon is crucial, and the maximum excitation of this strong surface plasmon mode can be achieved when excited by a Raman excitation laser at about 784 nm. This ensures ultimate sensitivity and very low detection limits when uses SERS for detection of target of interest, such as plant cells. In certain embodiments, when SERS detection is not required, the above specific limitation of the gold nanorod may not be necessary.

In one embodiment, the shell 106 is a silver layer. The silver layer 106 is coated on the AuNR 102 to form a silver coated gold nanorod (AuNR/Ag). In one embodiment, the AuNR 102 and the silver layer 106 have rough surfaces.

In one embodiment, the thickness of the silver layer 106 may be in the range of about 0.2-20 nm. In one embodiment, the thickness of the silver layer 106 is in the range of about 0.5-5 nm. In one embodiment, the thickness of the silver layer 106 is about 1-2 nm. In one embodiment, the thickness of the silver layer 106 is about 1.7 nm. The thin silver layer 106 helps maintain the longitudinal surface plasmon wavelength as close as possible to the excitation laser source (784 nm), in order to achieve the maximum SERS signal. Any thick silver coating will change the surface plasmon significantly. In certain embodiments, when SERS detection is not required, the above specific limitation of the silver layer thickness may not be necessary.

In one embodiment, the reporter layer 110 is a Raman reporter molecule layer having Raman reporter molecules. In one embodiment, the Raman reporter molecules are thiolated organic molecules absorbed on the surface of the AuNR/Ag. In one embodiment, the Raman reporter molecule may be at least one of 4-mercaptobenzoic acid (4MBA), p-aminothiophenol (PATP), p-nitrothiophenol (PNTP), 4-(methylsulfanyl) thiophenol (4MSTP), and other molecules with unique Raman spectra and intense Raman peak intensities. In other words, the one or more nanocomposites 100 of the nanoagent may include at least one of the following four types of nanocomposites: a nanocomposite having a 4MBA reporter layer, a nanocomposite having a PATP reporter layer, a nanocomposite having a PNTP reporter layer, and a nanocomposite having a 4MSTP reporter layer. In certain embodiments, the nanoagent may include all of these four types of nanocomposites 100. All the SER Raman spectra are obtained through the detection of those Raman reporter molecules.

In the above embodiment, the reporter molecule is a Raman reporter molecule. In certain embodiments, the reporter layer 110 may include other type of reporter molecules such that the produced nanoagent may be used together with detecting methods other than SERS, such as MRI, x-ray radiography, CT or IR. In certain embodiments, the reporter molecule is detectable by different methods. In certain embodiments, the report molecules may include one or more fluorescent agents. The one or more fluorescent agents can be quantum dots or fluorescent dyes. In certain embodiments, when detection of the nanocomposite is not necessary, the report molecule may not be required.

In the above embodiment, the nanoagent includes at least one of the four types of nanocomposites corresponding to four types of reporter molecules. In certain embodiments, the nanoagent may include all four types of nanocomposites. In certain embodiments, the nanoagent may include one, two, three, or more than four types of nanocomposites, and each type of nanocomposite has a special type of reporter molecule. In other embodiments, one type of nanocomposite may include two or more different types of reporter molecules. In certain embodiments, one type of nanocomposite may also include two, three, four or more types of reporter molecules.

In certain embodiments, the nanocomposite may not include the reporter layer 110. For example, if detection and monitoring of the target of interest have been done, or the detection and monitoring of the target of interest are not necessary, the nanocomposite does not have to include the reporter layer 110. In one embodiment, the binding layer 114 is directly applied to the shell layer 106.

In one embodiment, the binding layer 114 is applied to the surface of the SERS reporter molecule coated AuNR/Ag. In one embodiment, the binding layer 114 is a pegylated layer. In one embodiment, the pegylated layer may include thiolated PEG polymers, for example, at least one of HS-PEG, HS-PEG-COOH and HS-PEG-NHx, which are suitable for being used as SERS tags and are non-toxic. Additionally, the thiolated PEG polymers do not displace Raman reporter molecules, which attach to the surface of gold nanoparticles. In certain embodiments, the x in the HS-PEG-NHx is a positive integer. In one embodiment, x is 1 or 2.

In one embodiment, the pegylated layer 114 includes a mixture of HS-PEG and HS-PEG-COOH, which serves as protective, bio-dispersive and linker to the later conjugated targeting molecules, such as antibodies. In one embodiment, the average molecular weight of the HS-PEG is about 5 kD, and the average molecular weight of the HS-PEG-COOH is about 3 kD. In one embodiment, each nanorod (SERS reporter molecule coated AuNR/Ag) requires about 4,200 molecules to assure complete surface coverage, i.e. each HS-PEG molecule required 0.35 $nm^2$ footprint. The pegylated layer 114 may achieve at least two purposes. First, the pegylated layer 114 protects the nanorods surface and makes the nanocomposite more hydrophilic, and easily disperses the nanocomposite in aqueous medium, for example, biological fluids. Second, the pegylated layer 114 provides a carboxylic terminal on the surface of the SERS reporter molecule coated AuNR/Ag, which is the linker between the SERS reporter molecule coated AuNR/Ag surface and the antibodies that will attached thereon for targeting the target, such as cancer cells.

In certain embodiments, as described above, the pegylated layer 114 may be coated on the shell 106 directly, and the reporter layer 110 is not necessary. In one embodiment, the nanocomposite 100 does not include the pegylated layer 114 and the reporter layer 110, and the active layer 118 is directly attached to the shell 106.

In certain embodiments, the active layer 118 includes targeting molecules that specifically guide the nanoagent to the target of interest and specifically binds to the target of interest. In certain embodiments, the targeting molecule is an antibody. The antibody includes molecules of a type of antibody which specifically targeting certain plant cell surface antigen. In one embodiment, the antibody is attached covalently to HS-PEG-COOH (—COOH terminal) and plays a role in the specific SERS nanocomposite delivery to the plant cells.

In the above embodiment, the active layer 118 includes antibodies. In certain embodiments, the active layer 118 may include other type of targeting molecules to specifically binding an object, for example, a ligand that can bind a receptor, or a lectin that can bind a carbohydrate.

In certain embodiments, the nanoagent may not include the targeting molecules. The nanoagent may circulate in a plant, and thus is able to in contact with the target of interest. In one embodiment, the nanoagent is accumulated in the root of the plant after delivering to the plant.

In certain embodiments, the active layer 118 includes a bio-active agent and optionally targeting molecules. The bio-active agent and/or the targeting molecules may be attached to at least one of the shell 106, the reporter layer 110, or the binding layer 114. For example, the targeting molecules may be attached to certain amount of surfaces of the binding layer 114, while the bio-active agents occupy certain amount of surfaces of the binding layer 114. The targeting molecules and the bio-active agents altogether may occupy the complete surface of the binding layer 114 to have efficient binding and treating effects. In one embodiment, the targeting molecules and the bio-active agent altogether may only occupy parts of the outer surface of the binding layer, as long as the nanoagent provides efficient binding and treatment to the target of interest. In certain embodiments, the targeting molecules and the bio-active agent may be attached to each other by chemical bond, hydrophobic force, van der Waals force, or any other interaction forces, and at least one of the targeting molecule and the bio-active agent is attached to the binding layer 114. In one embodiment, the targeting molecules are attached to the binding layer 114 to form a first layer, and the bio-active agent is attached to the first layer of the targeting molecules to form a second layer of bio-active agent. Alternatively, the bio-active agent is attached to the binding layer 114 to form a first layer, and the targeting molecules are attached to the first layer of the bio-active agent to form a second layer of the targeting molecules. In other words, the active layer 118 may be implemented by a single layer or multiple layers. Further, at least a portion of the targeting molecules and a portion of the bio-active agent need to be exposed in the surface of the nanocomposite to efficiently fulfill their function. In other embodiments, at least a portion of the targeting molecules are exposed to ensure delivering of the nanocomposite to the target of interest, and during the delivering and after the delivering, the bio-active agent may be exposed or released to fulfill their function.

In certain embodiments, the bio-active agent is growth factor that induces certain biological functions, including the growth, proliferation of differentiation of cells or organisms. In one embodiment, the bio-active agent includes proteins, nucleic acids, drug molecules, virus, or a biological system that induces certain biological functions, the death of cells, tissues, or organisms.

In certain embodiments, the bio-active agent may also function as the targeting molecule, such that the bio-active agent not only specifically binds to the target of interest, but also interact with the target of interest to accomplish certain function.

In certain embodiments, at least one of the reporter layer 110 and the binding layer 114 is not present in the nanocomposite 100. The active layer 118 thus is attached to the shell 106, the reporter layer 110, the binding layer 114 or the targeting molecules of the active layer 118.

In the above embodiment, the nanoagent may include at least one of the four types of nanocomposites corresponding to four types of reporter molecules. In certain embodiments, the nanoagent may include all four types of nanocomposites. In certain embodiments, the nanoagent may include one, two, three, or more than four types of nanocomposites, and each type of nanocomposite has a specific type of reporter molecule. In other embodiments, one type of nanocomposite may include two or more different types of reporter molecules.

In one embodiment, the nanoagent as described above can be used to detect at least one specific type of cells in a plant, or at least one pathogen in a plant by SERS, treating the specific type of cells or the pathogen by the bio-active agent, and monitoring the conditions of the specific type of cell or the pathogen by SERS.

In certain embodiments, the nanoagent may be applied to the plant many times. The dosage and frequency of using the nanoagent may be determined according to the conditions of the plant.

After treatment by the bio-active agent of the nanoagent, the plant may grow faster than control plant that is not treated by the nanoagent. In certain embodiments, in addition to regulate growth or other properties of the plant, the nanoagent of the present invention also provides a convenient and accurate way to monitor the condition of the plant. In one embodiment, the conditions of the plant may be monitored at a predetermined time after each of the multiple treatments.

In certain embodiments, for cost effective treatment of the plant, the nanoagent may only include a nanostructure and a bio-active agent attached to the nanostructure. The nanostructure may be formed by a nanomaterial of quantum dots, nanowires, nanorods, nanotubes, nanofibers, fullerene, and silver coated gold nanorod, etc. In one embodiment, the nanomaterial is carbon nanotube. The bio-active agent may be a plant growth factor.

In one embodiment, the nanoagent includes Raman reporter molecules that are detectable by SERS. In certain embodiment, the nanoagent may include reporter molecules detectable by methods other than SERS, such as MRI, x-ray radiography, CT, or IR. The nanoagent is therefore configured to be applied with methods other than SERS, for specific targeting, detection, and treatment of the targeted cells, tissues or objects. In certain embodiments, the reporter molecules are detectable by two, three, four or more different methods described above.

In a further aspect, the present invention is directed to a method for regulating properties of a plant. FIG. 2 shows a flowchart of regulating properties of a plant according to one embodiment of the invention. As shown in FIG. 2, the method includes a plurality of operations. At operation 202, a nanoagent is provided. At operation 206, the nanoagent is delivered to a target plant or plant cells. Optionally at operation 210, the conditions of the target plant or plant cell can be detected or monitored.

The nanoagent may have the structure as described above. In certain embodiments, the nanoagent includes multiple nanocomposite. Each nanocomposite has a gold nanorod, a silver layer coated on an outer surface of the gold nanorod, a pegylated layer coated on the silver layer, an active layer conjugated to the pegylated layer. The silver layer includes silver nanoparticles. The pegylated layer includes at least one of thiolated polyethylene glycol (HS-PEG), thiolated polyethylene glycol acid (HS-PEG-COOH) and HS-PEG-NHx. The active layer includes at least one bio-active agent configured to interact with the plant. In one embodiment, the nanocomposite further includes a Raman reporter molecule layer disposed between the silver layer and the pegylated layer, as described above in regard to FIG. 1. The Raman reporter molecule layer has the Raman reporter molecules that are detectable by surface enhanced Raman spectroscopy (SERS). In one embodiment, the nanocomposite further includes a targeting layer conjugated to the pegylated layer, as described above in regard to FIG. 1. The targeting layer has at least one targeting molecule configured to bind to the plant.

In certain embodiments, the nanocomposite includes a nanostructure formed by a nanomaterial, and an active layer attached or conjugated to the nanostructure. The nanomaterial includes silver coated nanorods, quantum dots, nanowires, nanotubes, nanofibers, or fullerenes. In one embodiment, the nanomaterial is carbon nanotube, and the bio-active agent is 2,4-D.

In certain embodiments, the bio-active agent includes plant growth regulators, proteins, and nucleic acids. In certain embodiments, the bio-active agent is 2,4-dichlorophenoxyacetic acid (2,4-D) or other auxins, abscisic acid (ABA), cytokinins, ethylene, gibberellins, salicylic acid, nitric oxide, or jasmonates.

In certain embodiments, the step of delivering the nanoagent to the plant includes: providing a growing medium for plant cells of the plant to grow; seeding the plant cells in the growing medium; and adding the nanoagent to the growing medium.

In certain embodiment, the plant is tomato, tobacco, or cucumber.

EXAMPLES

Example 1: Effect of Silver Coated Nanord to Tomato Cells

Figure 3:
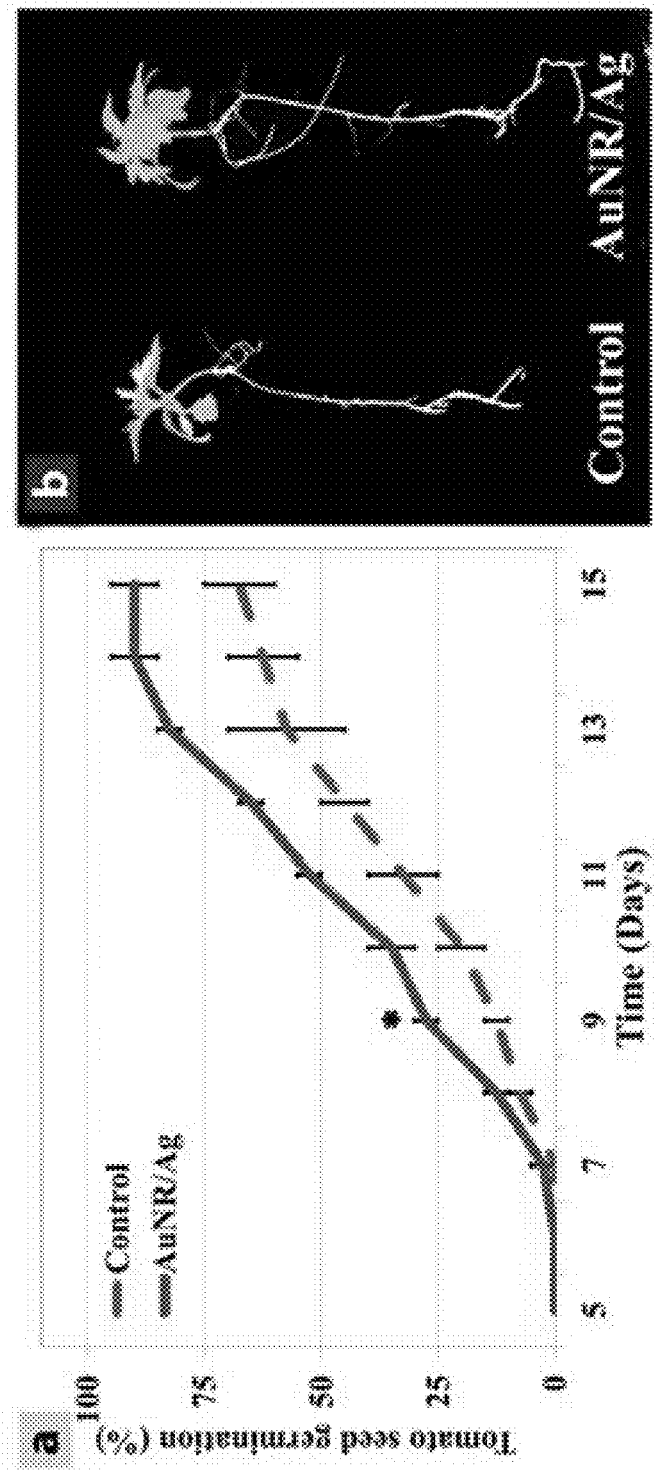
FIG. 3 shows effect of silver coated gold nanorod to seed germination of tomato cells according to one embodiment of the invention.

In this example, gold nanorods coated with silver (AuNR/Ag) are proved to not cause toxic effects to exposed young plants of tomato. An experiment is designed to focused on observing the germination of seeds exposed to AuNR/Ag by addition the nanoparticles directly to the medium. Synthesis of AuNR/Ag particles as well as attachment of 2,4-D were performed by Dr. Biris group (University of Arkansas at Little Rock). A detailed phenotypical analysis of germinated seedlings is further performed, as described previously. Seed germination was measured by monitoring the seeds daily for the appearance of the first root emergence as a sign of their germination. As shown in FIG. 3, AuNR/Ag included in the growing medium in a working concentration of 50 µg/ml did not affect the germination rate of tomato seeds, when compared to the controls. The germination rates for the seeds exposed to these AuNR/Ag were found to be slightly higher than those for the seeds growing on control medium, with a significant rate recorded on day 9 ($p=0.03$). As the next step, we monitored the development and growth of seedlings placed on a medium supplemented with AuNR/Ag and did not detect any symptoms of phytotoxicity or any negative effects on the development of AuNR/Ag exposed plants. The results show that seeds were able to grow and develop leaflets and maintain similar fresh and dry weight compared to controls.

FIG. 3 shows effect of silver coated gold nanorod to seed germination of tomato cells according to one embodiment of the invention. Referring to FIG. 3, seed germination and growth of tomato seedlings on MS medium supplemented with AuNR/Ag is disclosed. (a) shows percentage of tomato seeds germination and (b) shows phenotype of 21-day old seedling after growing on MS medium supplemented with AuNR/Ag at 50 µg/ml. Controls included seeds germinating on MS medium only ($p<0.05$, AuNR compared to control).

No previous study has investigated the phytotoxicity of silver-coated gold nanorods (AuNR/Ag). Additionally, studies related to understanding the effects of gold and silver nanoparticles are limited and sometimes contradictory (El-Temsak and Jones, 2012; Barrena et al., 2009). It has been shown that the size of the metal-based particles and their concentration in the growing medium are among the factors that can alter plant responses. For example, silver nanoparticles (2-20 nm in diameter) have been shown to have low to no phytotoxicity toward the germination and growth of cucumber, lettuce, and flax, when used at concentrations ranging from 20-116 µg/ml (El-Temsak and Jones, 2012; Barrena et al., 2009). Moreover, physiological investigation of gold nanorods on germination and growth of watermelon showed that these particles are able to increase seed germination and root elongation even at a high concentration of 200 µg/ml. In another study, the index of germination of cucumber and lettuce seeds increased when they were exposed to gold nanoparticles (20 nm in size at 20-116 µg/ml concentration). On the contrary, the negative effect of silver nanoparticles (5-100 nm in size) has been previously described (El-Temsak and Jones, 2012). Indeed, silver nanoparticles at concentrations of 100-1000 µg/ml and 100 nm in diameter were able to reduce zucchini biomass (57-71%) and germination and shoot length in barley (El-Temsak and Jones, 2012). Results of this example clearly demonstrated that AuNR/Ag can be easily absorbed by tomato plants without any inducing significant phytotoxic effects. Based on this fact, we decided to investigate the possibility of using the AuNR/Ag structures not only for their high-sensitivity detection in plant systems, but also to deliver a commonly used synthetic auxin growth regulator (2,4-dichlorophenoxyacetic acid (2,4-D)) to plant cells.

Example 2: Effect of Silver Coated Nanorod with 2,4-D to Tobacco Cells

Figure 4:
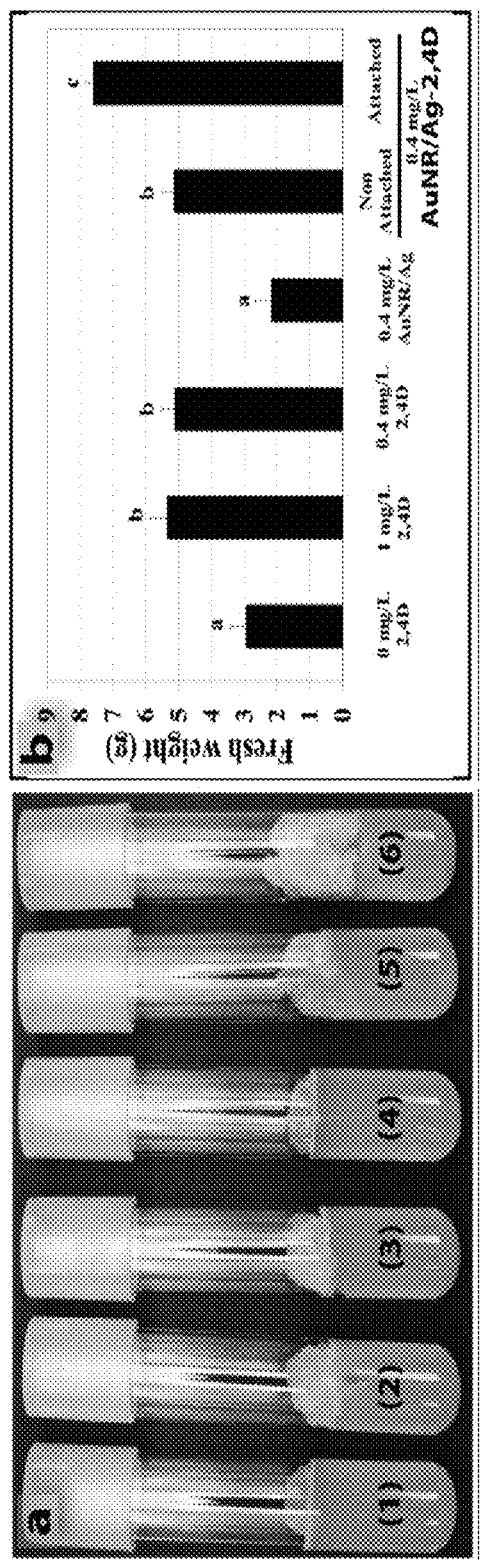
FIG. 4 schematically shows effect of silver coated gold nanorod/2,4D to tobacco callus growth according to one embodiment of the invention.

After 21 days of cultivation of the tobacco cells on MS media supplemented with AuNR/Ag-2,4-D conjugates, 2,4-D only, AuNR/Ag only, or AuNR/Ag+2,4-D as separate (non-attached) compounds, the biomass accumulation (fresh and dry weight) for all of these experimental conditions were estimated as shown in FIG. 4.

In FIG. 4, tobacco callus growth results after 21 days (fresh weight) are as follows: medium without 2,4-D (medium 1), medium with standard concentration of 2,4-D (1 mg/L) (medium 2), medium with 0.4 mg/L 2,4-D (medium 3), medium with 0.4 mg/L AuNR/Ag (medium 4), medium with individual (non-conjugated) 2,4-D (0.4 mg/L) and AuNR/Ag-2,4-D conjugates (0.4 mg/L) (medium 5), medium with AuNR/Ag-2,4-D conjugates (medium 6). The actual callus tubes are shown (a) and the corresponding fresh weight values are presented in (b).

As shown in FIG. 4, the addition of AuNR/Ag-2,4-D conjugates increased callus growth by 48% (±0.30 SE) compared to callus culture grown on medium supplemented with 2,4-D only. The addition of non-conjugated 2,4-D and AuNR/Ag to the growth medium did not cause any additional increase of biomass compared to medium supplemented with only 2,4-D. Non-conjugated AuNR/Ag nanoparticles were not found to stimulate or statistically impact the growth of callus compared with controls (medium without nanomaterials). These results provide clear indication that AuNR/Ag can promote biological activity of attached cell growth regulator (2,4-D) and, as a result, enhance the activation of cell growth caused by this bioactive compound.

It is well known that 2,4-D can promote cell division in tobacco (*Nicotiana tabacum*) culture cells. Moreover, this synthetic auxin can penetrate plant cells through different routes but mostly through the AUX 1 influx carrier. However, this transport inside cells was not described as active. The primary receptor of 2,4-D is the transport inhibitor response 1 (TIR1) (Parry et al., 2009). The active part of the 2,4-D molecule is the dichlorophenyl ring and the two chlorines of 2,4-D which go into the pocket of TIR1. Once 2,4-D binds to the TIR1 nuclear receptor, a ubiquitin-dependent degradation of Aux/IAA repressors is initiated and finally leads to the activation of the regulation of auxin-responsive genes. The increase of tobacco cell growth using AuNR/Ag-2,4-D conjugates could be associated with several possible pathways. First, the influx of 2,4-D inside tobacco cells could be increased by a higher uptake of nanorods associated with 2,4-D. Second, the attachment of 2,4-D to the nanorods by the carboxylic group could increase the ability of the halogenic groups to interact with the auxin receptor TIR1 cavity. Additional molecular investigations need to be conducted in order to understand the precise mechanism by which the conjugation of 2,4-D to AuNR/Ag can enhance the stimulation of tobacco cell growth. However, our current findings highlighted a multifunctional potential of gold nanoparticles in plant biology.

Certain embodiments of the present invention, among other things, have the following novel features.

1. Design of composition of gold nanomaterial that will allow specific growth regulator to attach to surface of nanomaterial. Optionally, particular layer of chemical compound may allow bond forming between nanomaterial and growth regulator.

2. Attachment of growth regulator to nanomaterial may be implemented using appropriate chemical reaction.

3. Delivery of conjugates to plants or plant cells or plant organ/tissue may be achieved.

4. Positive plant/cell response (increase of growth) may be assessed.

5. Monitoring of delivery of conjugate inside plant or cell may be performed using any method of detection (Raman spectroscopy, PA/PT, TEM).

Here, the first proof of the enhanced growth stimulation of plant cells (tobacco cell culture) is provided using gold nanoparticles as carrier for auxin growth regulator. Technologies designed for controlled delivery of bio-active molecules can be beneficial for areas of agriculture, horticulture as well as plant genetic engineering. It is proposed to use gold nanomaterial as carrier for delivery plant growth regulators of different chemical nature.

It is proved that gold nanoparticles can enhance the stimulating effect of 2,4-D in cell culture. It will be important to assess similar effect on level of whole plant organism.

This invention will dramatically increase productivity/yields of agricultural crops, bio-energy crops, plants used for production proteins, plastic and pharmaceuticals by more efficient delivery of growth regulators to commercially valuable plants.

In summary, plant growth regulators are routinely used for regulation of plant cell growth and development of mature plants. However, numbers of limitations of such approach exist. For example, hormonal plant regulators are not easily can be absorbed and move inside exposed plants. Thus, growth regulators can be less efficient in low doses but toxic for plants in higher doses. Additionally, ability of delivery of growth regulators to particular plant organ or tissue precisely is limited. Use of suitable nanomaterial as carrier for delivery of plant growth regulators can help to overcome discussed limitations. As shown in FIG. 4, potential of growth regulator (auxin 2,4-D in example) can be significantly increased if 2,4-D is attached to gold nanoparticles covered with silver layer. Thus, gold nanorods play a role of carries to auxin regulator.

In one embodiment, because the chemical structure of various growth regulators is different, investigator needs to find a way to attach particular growth regulator to various nanomaterial. In order to achieve it, nanomaterial should be covered with the substance that will allow the creation of the chemical bond between selected gold nanomaterial and specific growth regulator.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims as well as the invention including drawings.

RELATED PUBLICATIONS

Z. A. Nima, M. Mahmood, Y. Xu, T. Mustafa, F. Watanabe, D. A. Nedosekin, M. A. Juratli, T. Fahmi, E. I. Galanzha, J. P. Nolan, A. G. Basnakian, V. P. Zharov and A. S. Biris, *Sci. Rep.*, 2014, 4.

H. Villagarcia, E. Dervishi, K. de Silva, A. S. Biris and M. V. Khodakovskaya, *Small*, 2012, 8, 2328-2334.

Y. S. El-Temsah and E. J. Joner, *Environ. Toxicol.*, 2012, 27, 42-49.

R. Barrena, E. Casals, J. Colon, X. Font, A. Sánchez and V. Puntes, *Chemosphere*, 2009, 75, 850-857.3

G. Parry, L. I. Calderon-Villalobos, M. Prigge, B. Peret, S. Dharmasiri, H. Itoh, E. Lechner, W. M. Gray, M. Bennett and M. Estelle, *PNAS*, 2009, 106, 22540-22545.

What is claimed is:

1. A method for regulating properties of a plant, comprising
   providing a nanoagent having at least one nanocomposite; and
   delivering the nanoagent to the plant,
   wherein the nanocomposite comprises:
      at least one gold nanorod;
      a silver layer coated on an outer surface of the gold nanorod, the silver layer comprising silver nanoparticles;
      a pegylated layer coated on the silver layer, comprising at least one of thiolated polyethylene glycol (HS-PEG), thiolated polyethylene glycol acid (HS-PEG-COOH) and HS-PEG-NHx; and
      an active layer conjugated to the pegylated layer, the active layer comprising at least one bio-active agent configured to interact with the plant.

2. The method of claim 1, wherein the bio-active agent comprises plant growth regulators, proteins, and nucleic acids.

3. The method of claim 2, wherein the bio-active agent comprises 2,4-dichlorophenoxyacetic acid (2,4-D), abscisic acid (ABA), cytokinins, ethylene, gibberellins, salicylic acid, nitric oxide, or jasmonates.

4. The method of claim 1, wherein the step of delivering the nanoagent to the plant comprises:
providing a growing medium for plant cells of the plant;
seeding the plant cells in the growing medium; and
adding the nanoagent to the growing medium.

5. The method of claim 1, wherein the plant comprises tomato, tobacco, or cucumber.

6. The method of claim 1,
wherein the gold nanorod has an aspect ratio (AR) in a range of about 1-9, a length in a range of about 10-100 nm, and a diameter in a range of about 1-40 nm; and
wherein the silver layer has a thickness in a range of about 0.5-5 nm.

7. The method of claim 1,
wherein the nanocomposite further comprising a Raman reporter molecule layer disposed between the silver layer and the active layer; and
wherein the Raman reporter molecule layer comprises the Raman reporter molecules that are detectable by surface enhanced Raman spectroscopy (SERS).

8. The method of claim 7, wherein the Raman reporter molecule layer comprises 4-mercaptobenzoic acid (4MBA), p-aminothiophenol (PATP), p-nitrothiophenol (PNTP), 4-(methylsulfanyl) thiophenol (4MSTP), or other molecules with unique Raman spectra and intense Raman peak intensities.

9. The method of claim 8,
wherein the at least one nanocomposite comprises a first nanocomposite, a second nanocomposite, a third nanocomposite, and a fourth nanocomposite;
wherein the Raman reporter molecule layer of the first nanocomposite comprises 4-mercaptobenzoic acid (4MBA);
wherein the Raman reporter molecule layer of the second nanocomposite comprises p-aminothiophenol (PATP);
wherein the Raman reporter molecule layer of the third nanocomposite comprises p-nitrothiophenol (PNTP);
wherein the Raman reporter molecule layer of the fourth nanocomposite comprises 4-(methylsulfanyl) thiophenol (4MSTP); and
wherein SERS signal corresponding to each of the first, second, third and fourth nanocomposites is represented by a predetermined color.

10. The method of claim 1, wherein the HS-PEG has a molecular weight in a range of about 1.5-15 kilo Dalton (kD) and the HS-PEG-COOH has a molecular weight in a range of about 1-10 kD.

11. The method of claim 1, wherein the active layer further comprises a targeting molecule configured to bind to at least one cell of the plant.

12. A method for regulating properties of a plant, comprising:
providing a nanoagent having at least one nanocomposite; and
delivering the nanoagent to the plant,
wherein the nanocomposite comprises:
a nanostructure formed by at least one nanomaterial; and
an active layer conjugated to the nanostructure, comprising a bio-active agent.

13. The method of claim 12, wherein the bio-active agent comprises plant growth regulators, proteins, and nucleic acids.

14. The method of claim 13, wherein the bio-active agent comprises 2,4-dichlorophenoxyacetic acid (2,4-D), abscisic acid (ABA), cytokinins, ethylene, gibberellins, salicylic acid, nitric oxide, or jasmonates.

15. The method of claim 12, wherein the step of delivering the nanoagent to the plant comprises:
providing a growing medium for plant cells of the plant;
seeding the plant cells in the growing medium; and
adding the nanoagent to the growing medium.

16. The method of claim 12, wherein the plant comprises tomato, tobacco, or cucumber.

17. The method of claim 12, wherein the nanomaterial comprises at least one of silver coated gold rods, quantum dots, nanowires, nanotubes, nanofibers, and fullerenes.

* * * * *